United States Patent

Gutman

[11] 3,969,441
[45] July 13, 1976

[54] THIOALKYL PHOSPHONATES

[75] Inventor: Arnold D. Gutman, Berkeley, Calif.

[73] Assignee: Stauffer Chemical Company, Westport, Conn.

[22] Filed: Nov. 18, 1974

[21] Appl. No.: 524,906

Related U.S. Application Data

[62] Division of Ser. No. 298,979, Oct. 19, 1972, Pat. No. 3,862,999, which is a division of Ser. No. 123,467, March 11, 1971, abandoned.

[52] U.S. Cl. ................................................ 260/948
[51] Int. Cl.² ........................ C07F 9/40; C07F 9/44; A01N 9/36
[58] Field of Search ................................... 260/948

[56] References Cited
UNITED STATES PATENTS 3,074,991  1/1963  Schrader ............................ 260/948

FOREIGN PATENTS OR APPLICATIONS 1,039,456  8/1966  United Kingdom ................. 260/948

*Primary Examiner*—Anton H. Sutto
*Attorney, Agent, or Firm*—Edith A. Rice; Daniel C. Block

[57] ABSTRACT

New compounds having the generic formula:

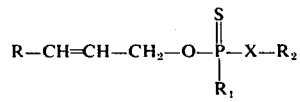

wherein R can be selected from the group consisting of hydrogen, alkyl and aryl; $R_1$ is alkyl; $R_2$ can be selected from hydrogen, alkyl, alkylcyano, thioalkyl, alkynyl, benzothiazolo, imidazolo, aryl and substituted aryl with the substituents being selected from nitro, alkyl, halogen, cyano, thioalkyl, haloalkyl and amido; X can be oxygen, sulfur or amino, provided that when X is oxygen or sulfur $R_2$ is other than hydrogen. Compounds of the present invention are active insecticides and miticides.

3 Claims, No Drawings

THIOALKYL PHOSPHONATES

This is a division of application Ser. No. 298,979 filed on Oct. 19, 1972, now U.S. Pat. No. 3,862,999 issued Jan. 28, 1975, which is a division application of Ser. No. 123,467 filed on Mar. 11, 1971 now abandoned.

DESCRIPTION OF THE INVENTION

This invention is directed to a novel group of compounds which may be generally described as phosphorous derivatives which are active insecticides and miticides. The compounds of the present invention are represented by the generic formula:

$$R-CH=CH-CH_2-O-\underset{\underset{R_1}{|}}{\overset{\overset{S}{\|}}{P}}-X-R_2$$

wherein R can be selected from the group consisting of hydrogen alkyl and aryl; $R_1$ is alkyl; $R_2$ can be selected from hydrogen, alkyl, alkylcyano, thioalkyl, alkynyl, benzothiazolo, imidazolo, aryl and substituted aryl with the substituents being selected from nitro, alkyl, halogen, cyano, thioalkyl, haloalkyl and amido; X can be oxygen, sulfur or amino, provided that when X is oxygen or sulfur $R_2$ is other than hydrogen.

In general, the above-noted compounds can be prepared by reacting an appropriate alcohol with ethylthionophosphine sulfide to form a reactive mercaptan. The mercaptan is then treated with a halide compound in the presence of a base such as triethylamine to form the end product. In the alternative, an appropriate alcohol can be reacted with a dihalothiophosphonous derivative to obtain a reactive thiochloridate phosphonous intermediate which is reacted with an appropriate compound to form the end product.

In order to illustrate the merits of the present invention, the following examples are provided.

EXAMPLE 1

O-crotyl-S-propargyl, ethylphosphonodithioate 12.4 grams (0.05 mole) of ethylthionophosphine sulfide is combined with 200 ml. of dioxane in a 600 ml. beaker. The mixture is stirred at room temperature and 7.2 grams (0.1 mole) of crotyl alcohol is added and the resulting mixture is stirred until a clear solution is obtained. The solution is cooled in an ice bath to 10°C. and 11.9 grams (0.1 mole) of propargyl bromide is added followed by the addition of 10.1 grams (0.1 mole) of triethylamine over a period of 10 minutes. The resulting mixture is stirred at room temperature for one hour, then poured into 300 mls. of benzene. The benzene mixture is washed with 200 ml. of water, 100 ml. of saturated sodium bicarbonate solution followed by two 100 ml. portions of water. The benzene phase is dried over anhydrous magnesium sulfate and evaporated under reduced pressure to yield 17.2 grams of product. $n_D^{30}$ - 1.5375.

EXAMPLE 2

O-allyl-O-ethylphosphorothiochloridate 54 g. (0.5 mole) of allyl alcohol, 56 g. (0.5 mole) of potassium t-butoxide and 500 ml. of tetrahydrofuran is combined and heated under reflux for one hour. The resulting solution is cooled to room temperature and is added over a period of one hour to a stirring solution of 89.5 g. (0.5 mole) of ethyldichlorothiophosphonate. The reaction temperature during the addition is maintained at −10° to −5°. After the addition is complete, the mixture is allowed to warm to room temperature and is stirred for one hour. The mixture is then poured into 500 ml. of benzene and washed with three 300 ml. portions of water. The benzene phase is dried with anhydrous $MgSO_4$ and evaporated under reduced pressure to yield 101 g. of the desired product. $n_D^{30}$ - 1.5347.

EXAMPLE 3

O-allyl-O-(3-methyl-4-nitrophenyl)-ethylphosphonothioate 9.2 grams (0.06 mole) of 3-methyl-4-nitrophenol is combined with 2.4 grams (0.06 mole) of caustic and 20 ml. of water in a 500 ml. three-necked flask fitted with a stirrer, thermometer, and dropping funnel. The mixture is stirred and 11.1 grams (0.06 mole) of the compound of Example 2 in 200 ml. of tetrahydrofuran is added over a period of 30 minutes. The resulting mixture is stirred and heated under reflux for two hours, cooled and poured into 400 ml. of benzene. The benzene mixture is washed with 200 ml. of water, 200 ml. of dilute caustic solution, followed by two 200 ml. portions of water. The benzene phase is dried with anhydrous $MgSO_4$ and evaporated under reduced pressure to yield 7.7 grams of product. $n_D^{30}$ - 1.5380.

Other compounds were prepared in an analogous manner starting with the appropriate materials as outlined above. The following is a table of compounds representative of those embodied by the present invention. Compound numbers have been assigned to them and are used for identification throughout the balance of the specification.

TABLE I $$R-CH=CH-CH_2-O-\underset{\underset{R_1}{|}}{\overset{\overset{S}{\|}}{P}}-X-R_2$$

| Compound No. | X | R | $R_1$ | $R_2$ |
|---|---|---|---|---|
| 1 | S | $CH_3$ | $C_2H_5$ | $CH_2-C≡CH$ |
| 2 | S | $CH_3$ | $C_2H_5$ | $CH_2-SC_2H_5$ |
| 3 | S | $CH_3$ | $C_2H_5$ | $CH_2-C≡N$ |
| 4 | S | H | $C_2H_5$ | $CH_2-C≡CH$ |
| 5 | S | H | $C_2H_5$ | $CH_2-C≡N$ |
| 6 | S | H | $C_2H_5$ | $CH_2-SC_2H_5$ |
| 7 | S | C$_6$H$_5$ | $C_2H_5$ | $CH_2-C≡N$ |
| 8 | S | C$_6$H$_5$ | $C_2H_5$ | $CH_2-C≡CH$ |
| 9 | O | $CH_3$ | $C_2H_5$ | 4-$NO_2$-C$_6$H$_4$ |
| 10 | O | $CH_3$ | $C_2H_5$ | 3-$CH_3$-4-$NO_2$-C$_6$H$_3$ |

TABLE I-continued $$R-CH=CH-CH_2-O-\overset{\overset{\displaystyle S}{\|}}{\underset{R_1}{P}}-X-R_2$$

| Compound No. | X | R | $R_1$ | $R_2$ |
|---|---|---|---|---|
| 11 | S | $CH_3$ | $C_2H_5$ | –C₆H₄–Cl (4-Cl) |
| 12 | O | $CH_3$ | $C_2H_5$ | –C₆H₄–CN (4-CN) |
| 13 | O | $CH_3$ | $C_2H_5$ | 2,4,5-trichlorophenyl |
| 14 | O | $CH_3$ | $C_2H_5$ | –C₆H₄–Cl (4-Cl) |
| 15 | S | H | $C_2H_5$ | –C₆H₄–Cl (4-Cl) |
| 16 | O | H | $C_2H_5$ | 2-methyl-4-nitrophenyl |
| 17 | S | H | $C_2H_5$ | –C₆H₅ |
| 18 | S | $CH_3$ | $C_2H_5$ | –C₆H₅ |
| 19 | S | $CH_3$ | $C_2H_5$ | –C₆H₄–Br (4-Br) |
| 20 | O | $CH_3$ | $C_2H_5$ | 2,4,5-trichlorophenyl |
| 21 | O | H | $C_2H_5$ | –C₆H₄–CN (4-CN) |
| 22 | O | H | $C_2H_5$ | –C₆H₄–NO₂ (4-NO₂) |
| 23 | O | H | $C_2H_5$ | 2-methyl-4-chlorophenyl |
| 24 | S | H | $C_2H_5$ | –C₆H₄–Br (4-Br) |
| 25 | O | $CH_3$ | $C_2H_5$ | 2-methyl-4-chlorophenyl |
| 26 | S | H | $C_2H_5$ | –C₆H₄–CH₃ (4-CH₃) |
| 27 | O | $CH_3$ | $C_2H_5$ | –C₆H₄–CF₃ |
| 28 | O | H | $C_2H_5$ | –C₆H₄–SCH₃ |
| 29 | O | H | $C_2H_5$ | 2,4,5-trichlorophenyl |
| 30 | O | H | $C_2H_5$ | –C₆H₄–CF₃ |
| 31 | O | H | $C_2H_5$ | 3,4-dichlorophenyl |
| 32 | O | H | $CH_3$ | –C₆H₄–NO₂ (4-NO₂) |
| 33 | O | H | $CH_3$ | 2-methyl-4-nitrophenyl |
| 34 | S | H | $CH_3$ | –C₆H₅ |
| 35 | S | H | $CH_3$ | –C₆H₄–Cl (4-Cl) |
| 36 | O | $CH_3$ | $CH_3$ | –C₆H₄–NO₂ (4-NO₂) |
| 37 | O | $CH_3$ | $CH_3$ | 2-methyl-4-nitrophenyl |

TABLE I-continued $$R-CH=CH-CH_2-O-\overset{\underset{\displaystyle R_1}{\|}}{\underset{}{P}}(S)-X-R_2$$

| Compound No. | X | R | $R_1$ | $R_2$ |
|---|---|---|---|---|
| 38 | S | $CH_3$ | $CH_3$ |  |
| 39 | S | $CH_3$ | $CH_3$ |  —Cl |
| 40 | S | $CH_3$ | $CH_3$ |  —Br |
| 41 | S | $CH_3$ | $CH_3$ |  —$CH_3$ |
| 42 | S | H | $CH_3$ |  —Br |
| 43 | S | H | $CH_3$ |  —$CH_3$ |
| 44 | NH | $CH_3$ | $C_2H_5$ | H |
| 45 | NH | $CH_3$ | $C_2H_5$ | $CH_3$ |
| 46 | O | $CH_3$ | $CH_3$ | $CH_2C\equiv CH$ |
| 47 | S | $CH_3$ | $C_2H_5$ |  |
| 48 | S | H | $C_2H_5$ |  |
| 49 | S | H | $C_2H_5$ |  |
| 50 | O | H | $C_2H_5$ |  |
| 51 | S | $CH_3$ | $CH_3$ |  |
| 52 | O | H | $CH_3$ |  |
| 53 | O | $CH_3$ | $CH_3$ |  |

TABLE I-continued $$R-CH=CH-CH_2-O-\overset{\underset{\displaystyle R_1}{\|}}{\underset{}{P}}(S)-X-R_2$$

| Compound No. | X | R | $R_1$ | $R_2$ |
|---|---|---|---|---|
| 54 | O | H | $CH_3$ |  —CN |
| 55 | O | $CH_3$ | $CH_3$ |  |
| 56 | O | $CH_3$ | $CH_3$ | 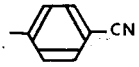 —CN |
| 57 | O | $CH_3$ | $CH_3$ |  |
| 58 | O | $CH_3$ | $CH_3$ | 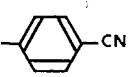 |
| 59 | O | H | $CH_3$ | 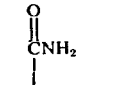 |

ENTOMOLOGICAL TESTING METHODS

I. House Fly [*Musca domestica* (L.)]

A stock solution containing 100 μg/ml of the toxicant in an appropriate solvent is prepared. Aliquots of this solution are combined with one ml. of an acetone-peanut oil solution in a dish, 55 mm in diameter, and allowed to dry. The aliquots are varied to achieve desired toxicant concentrations ranging from 100 μg per dish to that at which 50% mortality is obtained. The dishes are placed in a circular cardboard cage, closed on the bottom with cellophane and covered on top with cloth netting. Twenty-five female house flies are introduced into the cage and the percent mortality is recorded after 48 hours. LD-50 values are expressed in terms of μg per 25 female flies.

II. German Cockroach [*Blattella germanica* (Linné)]

Ten one-month old nymphs are placed into a circular cardboard cage sealed on one end with cellophane and covered by cloth netting on the other. Aliquots of the toxicant, dissolved in an appropriate solvent, are diluted in water to which has been added 0.0002% of a conventional wetting agent such as polyoxyethylene sorbitan monolaurate ether of alkylated phenols blended with organic sulfonates. Test concentrations range from 0.1% to that at which 50% mortality is obtained. Each of these aqueous suspensions are sprayed onto the insects, through the cloth netting, by means of a hand spray gun. Percent mortality is recorded after 72 hours and the LD-50 values are expressed as percent of toxicant in the aqueous spray.

III. Lygus Bug [*Lygus hesperus* (Knight)]

Same as for the German cockroach (II) except that the test concentrations range from 0.05% to that at which 50% mortality is obtained.

IV. Salt-marsh Caterpillar [*Estigmene acrea* (Druryl)]

Test solutions are prepared in an identical manner and concentrations are the same as those for the German cockroach (II). Sections of bitter dock (*Rumex obtusifolius*) leaves, 1–1.5 inches in length are immersed in the test solutions for 10–15 seconds and placed on a wire screen to dry. The dried leaf is placed on a moistened piece of filter paper in a petri dish and infested with five third-instar larvae. Mortality of the larvae is recorded after 72 hours and the LD-50 values are expressed as percent acitve ingredient in the aqueous suspensions.

V. Beet Armyworm [*Spodoptera exigua* (Hübner)]

Same as salt-marsh caterpillar (IV) except that leaves of Romaine lettuce (*Latuca sativa*) are used as the host plant.

VI. Tobacco Budworm [*Heliothis virescens* (F.)]

Same as for Beet armyworm (V).

VII. Black bean Aphid [*Aphis fabae* (Scop.)]

Nasturtium (*Tropaeolum* sp.) plants, approximately 2–3 inches tall, are transplanted into sandy loam soil in 3-inch clay pots and infested with 50–75 aphids of mixed ages. Twenty-four hours later they are sprayed, to the point of runoff, with aqueous suspensions of the toxicant. The suspensions are prepared as in previously described tests. Test concentrations ranged from 0.05% to that at which 50% mortality is obtained. Mortality is recorded after 48 hours and the LD-50 values are expressed as percent active ingredient in the aqueous suspensions.

VIII. Two-spotted Mite [*Tetranychus urticae* Koch)]

Same as for the black bean aphid (VII) except that pinto beans (Phaseolus sp.) are utilized as the host plant rather than nasturtiums.

IX. Systemic Tests

A. Black bean aphid:

Aliquots of the toxicant dissolved in an appropriate solvent are incorporated into 1 pound samples of sandy loam soil and placed into 1 pint ice-cream cartons. Test concentrations range from 10 ppm of toxicant per pound of soil down to that at which 50% mortality is obtained. Nasturtium (Tropaeolum sp.) plants approximately 2–3 inches tall are transplanted into the treated soil and infested with 50–75 aphids of various ages. Mortality is recorded 72 hours after infestation, and LD-50 values are expressed as ppm of active ingredient per pound of soil.

B. Two-spotted mite:

Preparation of the test solution and concentrations is the same as for the salt-march caterpillar test. Pinto bean (Phaseolus sp.) plants with expanded primary leaves are placed in the solution so that the roots and major portions of the stem are completely immersed. Immediately after, the leaves are infested with 75–100 mites of various ages. Mortality of adults, nymphs and eggs is recorded after one week, and LD-50 values are expressed as ppm of toxicant in the aqueous suspensions.

TABLE II

| Compound No. | HF μg | GR % | LB % | BA % | BAS ppm | SMC % | BAW % | TBW % | Two-Spotted Mites PE % | Eggs % | Sys % |
|---|---|---|---|---|---|---|---|---|---|---|---|
| 1 | 5 | .03 | .005 | .003 | 10 | .03 | .03 | .01 | .03 | >.05 | >10 |
| 2 | 7 | .03 | .003 | .003 | 5 | .01 | .03 | .03 | .03 | >.05 | >10 |
| 3 | 8 | .03 | .005 | .001 | 10 | .1 | .1 | .01 | .03 | >.05 | >10 |
| 4 | 7 | .05 | .01 | .03 | 3 | .03 | .01 | .03 | .005 | >.05 | 3 |
| 5 | 7 | .03 | .001 | .003 | .8 | .03 | .03 | .003 | .005 | .05 | .8 |
| 6 | 10 | .03 | .008 | .003 | 3 | .08 | .01 | .008 | .001 | .03 | .3 |
| 7 | 100 | >.1 | >.05 | .05 | | >.1 | >.1 | | .01 | >.05 | >10 |
| 8 | 30 | >.1 | >.05 | >.05 | | >.1 | >.1 | | .03 | >.05 | >10 |
| 9 | 5 | .003 | .003 | .0003 | 8 | .01 | .008 | .03 | .01 | >.05 | >10 |
| 10 | 7 | .01 | .003 | .003 | >10 | .1 | .01 | .01 | .01 | >.05 | >10 |
| 11 | 30 | .08 | .03 | .003 | >10 | .03 | .03 | .01 | .03 | .05 | >10 |
| 12 | 6 | .03 | .003 | .001 | >10 | .05 | >.1 | .01 | .01 | >.05 | >10 |
| 13 | 30 | >.1 | .03 | .001 | >10 | .08 | >.1 | .05 | .05 | >.05 | >10 |
| 14 | 30 | .1 | >.05 | .03 | >10 | >.1 | .1 | .03 | >.05 | >.05 | |
| 15 | 20 | .01 | .005 | .005 | 8 | .005 | .01 | .001 | .03 | >.05 | >10 |
| 16 | 15 | .01 | .003 | .001 | 3 | .003 | .01 | .005 | >.05 | >.05 | |
| 17 | 30 | .03 | .008 | .003 | 3 | .005 | .008 | .005 | .008 | >.05 | >10 |
| 18 | 50 | .05 | .03 | .001 | >10 | .05 | .03 | .03 | .03 | >.05 | >10 |
| 19 | 50 | .1 | .05 | .008 | >10 | .1 | | | .03 | >.05 | >10 |
| 20 | 30 | >.1 | .05 | .0008 | 8 | .03 | .05 | .05 | .03 | >.05 | >10 |
| 21 | 15 | .03 | .003 | .003 | 5 | .03 | .003 | .03 | .01 | >.05 | .8 |
| 22 | 5 | .005 | .001 | .0003 | 3 | .03 | .001 | .003 | .01 | >.05 | |
| 23 | 50 | >.1 | >.05 | >.05 | | >.1 | | | >.05 | >.05 | |
| 24 | 30 | .03 | .01 | .008 | >10 | .05 | .03 | .03 | .03 | >.05 | >10 |
| 25 | 40 | >.1 | | .03 | >10 | >.1 | >.1 | .1 | .03 | >.05 | >10 |
| 26 | 20 | .03 | .005 | .003 | >10 | .03 | .03 | .03 | .05 | >.05 | >10 |
| 27 | 15 | .1 | .05 | .008 | 8 | .1 | .1 | .05 | .03 | >.05 | 10 |
| 28 | 30 | .03 | .005 | .003 | 8 | >.1 | .08 | .01 | .008 | .05 | 3 |
| 29 | 50 | .08 | .01 | .0008 | 8 | .03 | .03 | .03 | .01 | >.05 | >10 |
| 30 | 30 | >.1 | >.05 | >.05 | | >.1 | >.1 | >.1 | >.05 | >.05 | |
| 31 | 30 | .1 | >.05 | .03 | >10 | .08 | .05 | .05 | .03 | >.05 | >10 |
| 32 | 8 | .008 | .0005 | .0005 | 3 | .01 | .003 | .05 | .003 | >.05 | >10 |
| 33 | 8 | .03 | .003 | .001 | 3 | .03 | .003 | .003 | .005 | >.05 | >10 |
| 34 | 30 | .03 | .003 | .0008 | 3 | .008 | .01 | .03 | .005 | >.05 | 3 |
| 35 | 30 | .01 | .001 | .001 | 3 | .003 | .001 | .01 | .005 | >.05 | >10 |
| 36 | 8 | .003 | .003 | .0003 | 3 | .01 | .03 | .01 | .008 | >.05 | >10 |
| 37 | 9 | .005 | .008 | .0003 | 3 | .03 | .003 | .005 | .005 | .03 | >10 |
| 38 | 45 | .03 | .01 | .001 | 8 | .01 | .01 | .03 | .01 | >.05 | >10 |
| 39 | 25 | .01 | .03 | .003 | 3 | .03 | .003 | .008 | .03 | >.05 | >10 |
| 40 | 30 | .03 | .03 | .003 | >10 | .03 | .01 | .03 | .03 | >.05 | >10 |
| 41 | 30 | .08 | .03 | .008 | 8 | .03 | .03 | .08 | .01 | >.05 | >10 |
| 42 | 25 | .03 | .003 | .008 | 3 | .008 | .003 | .03 | .003 | >.05 | >10 |

TABLE II-continued

| Compound No. | HF μg | GR % | LB % | BA % | BAS ppm | SMC % | BAW % | TBW % | Two-Spotted Mites PE % | Eggs % | Sys % |
|---|---|---|---|---|---|---|---|---|---|---|---|
| 43 | 25 | .03 | .003 | .008 | 3 | .008 | .03 | .01 | .008 | >.05 | >10 |
| 44 | 30 | .1 | .05 | .003 | 3 | >.1 | >.1 | >.1 | .03 | >.05 | 1 |
| 45 | 100 | .1 | >.05 | .03 | 3 | >.1 | | | >.05 | >.05 | |
| 46 | 90 | .08 | .03 | .008 | 1 | .1 | >.1 | .1 | .05 | >.05 | 3 |
| 47 | 30 | >.1 | | .008 | 3 | >.1 | >.1 | .1 | .05 | >.05 | 8 |
| 48 | >100 | >.1 | >.05 | .03 | 9 | .1 | | >.1 | .03 | >.05 | >10 |
| 49 | >100 | | | >.05 | | >.1 | | | >.05 | >.05 | |
| 50 | >100 | | | >.05 | | >.1 | | | >.05 | >.05 | |
| 51 | >100 | | | >.05 | | >.1 | | | >.05 | >.05 | |
| 52 | 50 | >.1 | >.05 | .03 | 8 | >.1 | >.1 | >.1 | >.05 | >.05 | |
| 53 | 20 | .05 | .001 | .0003 | 3 | .03 | .05 | .01 | | | >10 |
| 54 | 5 | .008 | .003 | .001 | 3 | .03 | .003 | .01 | | | |
| 55 | 30 | >.1 | .05 | .003 | 10 | >.1 | | | | | >10 |
| 56 | 5 | .005 | .003 | .0008 | 3 | .03 | .08 | .008 | | | >10 |
| 57 | 90 | >.1 | >.05 | .003 | 5 | >.1 | >.1 | >.1 | | | >10 |
| 58 | 15 | >.1 | >.05 | .003 | 3 | .08 | .05 | .03 | | | >10 |
| 59 | 40 | >.1 | .03 | .001 | 3 | .08 | .08 | .03 | >.05 | >.05 | |

What is claimed is:
1. Compounds corresponding to the formula

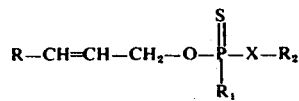

wherein R is selected from the group consisting of hydrogen, alkyl and aryl; $R_1$ is alkyl; $R_2$ is thioalkyl; X is oxygen, sulfur or amino.

2. A compound as set forth in claim 1 wherein X is S, R is $CH_3$, $R_1$ is $C_2H_5$ and $R_2$ is $CH_2-SC_2H_5$.

3. A compound as set forth in claim 1 wherein X is S, R is H, $R_1$ is $C_2H_5$ and $R_2$ is $CH_2-SC_2H_5$.

* * * * *